US 6,558,337 B2

(12) United States Patent
Dvorak et al.

(10) Patent No.: US 6,558,337 B2
(45) Date of Patent: May 6, 2003

(54) POSITIONER FOR MEDICAL DEVICES SUCH AS BIOPSY NEEDLES

(75) Inventors: Eric Maitland Dvorak, Madison, WI (US); Justin Edward Kolterman, Madison, WI (US); William Christopher Andrae, Madison, WI (US); Frederick Kelcz, Madison, WI (US); Frank J. Fronczak, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/836,025

(22) Filed: Apr. 17, 2001

(65) Prior Publication Data

US 2002/0151820 A1 Oct. 17, 2002

(51) Int. Cl.[7] .............................................. A61B 19/00
(52) U.S. Cl. ..................... 600/564; 606/130; 606/167
(58) Field of Search ................... 600/562, 564, 600/567, 568; 606/130, 167

(56) References Cited

U.S. PATENT DOCUMENTS

| 5,078,142 A | * | 1/1992 | Siczek et al. ............. 378/37 |
| 5,409,497 A | * | 4/1995 | Siczek et al. ............ 378/162 |
| 5,735,264 A | * | 4/1998 | Siczek et al. ............ 600/408 |
| 5,769,086 A | * | 6/1998 | Ritchart et al. ........... 600/566 |
| 5,776,062 A | * | 7/1998 | Nields ...................... 128/915 |
| 5,833,627 A |   | 11/1998 | Ascher et al. |
| 5,913,863 A |   | 6/1999 | Fischer et al. |
| 5,993,463 A |   | 11/1999 | Truwit |

FOREIGN PATENT DOCUMENTS

| WO | WO 93 17620 A | 9/1993 |
| WO | WO 96 08199 A | 3/1996 |

* cited by examiner

Primary Examiner—Stephen M. Hepperle
(74) Attorney, Agent, or Firm—Craig A. Frieschko, Esq.; DeWitt Ross & Stevens S.C.

(57) ABSTRACT

A positioner for centering or otherwise situating medical devices such as biopsy needles with respect to a human body includes a clamp for receiving a portion of the human body (e.g., a breast), a carriage which moves along a carriage path next to the clamp, and a positioning arm pivotally mounted to the carriage and having a mount for a medical device thereon. The carriage may therefore carry the positioning arm along the carriage path to a desired location adjacent to the clamp, at which point the positioning arm may be pivoted to situate a medical device within the device mount at a desired location adjacent the portion of the body within the clamp. The components of the positioner are preferably made of materials that do not interfere with medical imaging instrumentation (e.g., MRI scanners), though the positioner may include markers at desired locations (e.g., on the positioning arm adjacent the device mount) which are visible by the imaging instrumentation so that the location of the medical device may be ascertained during imaging.

32 Claims, 2 Drawing Sheets

POSITIONER FOR MEDICAL DEVICES SUCH AS BIOPSY NEEDLES

FIELD OF THE INVENTION

This disclosure generally concerns apparata used to center or otherwise position medical devices with respect to the human body during medical procedures, and more specifically concerns such positioning apparata which are sized and configured to allow their use within close spatial confines, e.g., within the interior of a magnetic resonance imaging (MRI) device.

BACKGROUND OF THE INVENTION

It is often necessary to position a medical device, such as a biopsy needle, adjacent to a portion of the human body during a medical imaging procedure, such as magnetic resonance imaging (MRI). Using MRI as an example, doctors are now commonly using MRI to locate breast tumors for biopsy prior to surgery. The current process uses a clamp which holds the patient's breast in place while the MRI scan is done. Once the breast (and the tumor therein) is imaged, the patient is removed from the MRI machine and the tumor's coordinates within the breast are calculated from the MRI scan. Medical personnel then make use of a positioning device, generally some form of linkage which bears a mount capable of holding a medical device or pointer, and which may position the device/pointer in two or more dimensions. The positioning device is situated adjacent to the breast and its device mount is manually aligned with the tumor to the best of the aligner's ability. The patient is then put back into the MRI device and re-scanned to see if the device mount of the positioner is properly aligned with respect to the tumor. If misaligned, the patient is withdrawn, the positioner is adjusted to more accurately align the device mount with the tumor, and the patient is scanned again. The process is repeated until the positioner has the mount accurately aligned with the tumor. A needle is then placed in the aligned device mount to penetrate the tumor. Often, the process requires four or five iterations of aligning the positioner's device mount with the tumor, with these iterations taking over an hour to perform.

An exemplary positioner of the type noted above is marketed by MRI Devices of Waukesha, Wis. (USA). This positioner utilizes a breast clamp defined by parallel plates having variable spacing so that the plates can be moved to engage the breast. One of the plates has an arch-like shape so that the portion of the plate surrounding the inner curve of the arch holds the breast in place, but a portion of the breast is left exposed within the curve of the arch. The clamp is situated on a positioner base which also bears a sliding carriage. The sliding carriage may be manually situated at a selected position along a path situated parallel to the arched plate of the clamp. The carriage bears a vertical arm which extends perpendicular to the carriage path and parallel to the arched plate. A medical device mount is slidably mounted on the arm so that the mount (and any medical device therein) may be manually positioned vertically on the arm, while the arm's carriage may be horizontally located at a desired position. Thus, medical personnel may manually situate the medical device in 2 degrees of freedom, within a plane oriented parallel to the arched plate, and therefore with respect to the portion of the human body maintained within the clamp.

While the positioner works well in the procedure noted above, the iterative procedure for locating the device mount with respect to the tumor requires significant personnel time and equipment time, making the procedure expensive. Additionally, the time required for the procedure adds to the patient's fear and discomfort, since the patient's body is maintained in the clamp for a substantial period of time as the patient awaits a potentially painful procedure. Therefore, there is a need for a positioner which allows faster tumor location procedures than those provided by prior positioners.

SUMMARY OF THE INVENTION

The invention involves a positioner for medical devices which is intended to at least partially solve the aforementioned problems. To give the reader a basic understanding of some of the advantageous features of the invention, following is a brief summary of a preferred version of the positioner. As this is merely a summary, it should be understood that more details regarding the preferred version may be found in the Detailed Description set forth elsewhere in this document. The claims set forth at the end of this document then define the various versions of the invention in which exclusive rights are secured.

An exemplary positioner (as illustrated in the accompanying Figures) includes a clamp (element 16 in conjunction with elements 18 and 20) for a selected portion of a human body (e.g., a breast); a carriage (element 22) which moves along a carriage path (element 24) next to the clamp, and a positioning arm (element 26) pivotally mounted to the carriage and having a mount (element 30 in FIG. 1) for a medical device thereon. The carriage may therefore carry the positioning arm along the carriage path to a desired location adjacent to the clamp, at which point the positioning arm may be pivoted to situate a medical device (e.g., a biopsy needle) within the device mount to a desired location adjacent the portion of the body within the clamp. The components of the positioner are preferably made of materials that do not interfere with medical imaging instrumentation such as MRI scanners. However, the positioner may include markers at desired locations, such as within the device mount or on the positioning arm adjacent the device mount, which are visible by the imaging instrumentation so that the location of the medical device may be ascertained during imaging.

The clamp includes two or more grasping elements with adjustable spacing so that some or all of the grasping elements can be brought to bear upon the portion of the human body to be subjected to the medical and/or imaging procedure. As an example, the clamp may include first and second grasping elements, such as a pair of plates (one being shown at element 16 and the other being defined by elements 18 and 20 in conjunction), wherein the second grasping element is movable toward the first grasping element along a grasping direction to secure the extremity between the elements. The first grasping element, which preferably remains fixed in a plane adjacent to the carriage path, may include first and second members (18 and 20) which are repositionable within that plane so that the spacing between the members can be varied, thereby effectively defining a gap within the first grasping element with the gap having variable spacing. Thus, when the extremity is grasped between the first and second grasping elements, the first grasping element's first and second members can be spaced so as to comfortably grasp the extremity while leaving the gap between the members through which the extremity may be accessed. Thus, a medical device borne on the carriage to a location adjacent the first grasping element can access the extremity through the gap. In the preferred version of the invention shown in the Figures, the first grasping element includes members provided in the form of a pair of bars carried within tracks at their opposing ends so that the bars may be slidably repositioned with respect to each other, and the second grasping element is a plate which is carried towards the bars on one or more tracks (e.g., screw drives) which maintain the second grasping element in the same orientation as it moves towards the bars (as by maintaining the second grasping element parallel to a plane defined by the first and second bars).

The carriage may be provided in the form of a plate which translates along a carriage path defined by a track or other structure located adjacent to the clamp. Preferably, where the clamp is formed of a pair of grasping elements which fit about the extremity, the carriage translates along a carriage path which is oriented perpendicular to the grasping direction (the direction in which the grasping elements travel to grasp the extremity). Thus, where the carriage travels adjacent to a first grasping element which includes the first and second members (e.g., sliding bars) noted previously, the carriage may slide along the length of the gap defined between the members to allow the medical device access to a desired portion of the extremity maintained against the members.

The positioning arm includes a pivot (element 28 in the Figures) at which the positioning arm is rotatably mounted to the carriage, and the medical device mount is spaced from the pivot, preferably at an end of the positioning arm. The positioning arm may rotate about the pivot to swing adjacent to the clamp, preferably in a plane parallel and adjacent to the first grasping element of the clamp (and parallel and adjacent to the first and second members therein), so that the medical device mounted on the positioning arm is positionable in various locations with respect to the clamp. This plane in which the positioning arm swings is preferably coincident with the carriage path so that the motion of the carriage may partially complement the motion of the positioning arm.

The clamp is preferably mounted on a positioner base (element 38) upon which the carriage also slides, with the positioner base (as well as the clamp and the carriage) being sized so that it may be easily lifted, carried, and positioned by a single person. In particular, it is preferably sized so that it may fit adjacent to a patient situated within the tight confines of an MRI device. In such tight confines, the aforementioned sliding carriage and pivoting positioning arm arrangement—wherein the carriage slides along the plane in which the positioning arm swings, this plane being situated adjacent the clamp—is highly advantageous because the medical device mounted in the positioning arm may be positioned in a wide variety of locations, but the structure required to provide such positioning need not occupy substantial space. Actuation of the positioning arm on the carriage is preferably provided by rotatably driving the positioning arm with an elongated driving link (element 52) which moves with respect to the carriage. Most preferably, the driving link is formed as a toothed rack which drives a pinion connected to the positioning arm. The rack is preferably driven on the carriage by a fluid actuator (e.g., a hydraulic cylinder), and the carriage is preferably similarly driven with respect to the positioner base, with manual or automatic control of the actuators being possible.

Further advantages, features, and objects of the invention will be apparent from the following detailed description of the invention in conjunction with the associated drawings.

DETAILED DESCRIPTION OF PREFERRED EMBODIMENTS OF THE INVENTION

Figure 1:
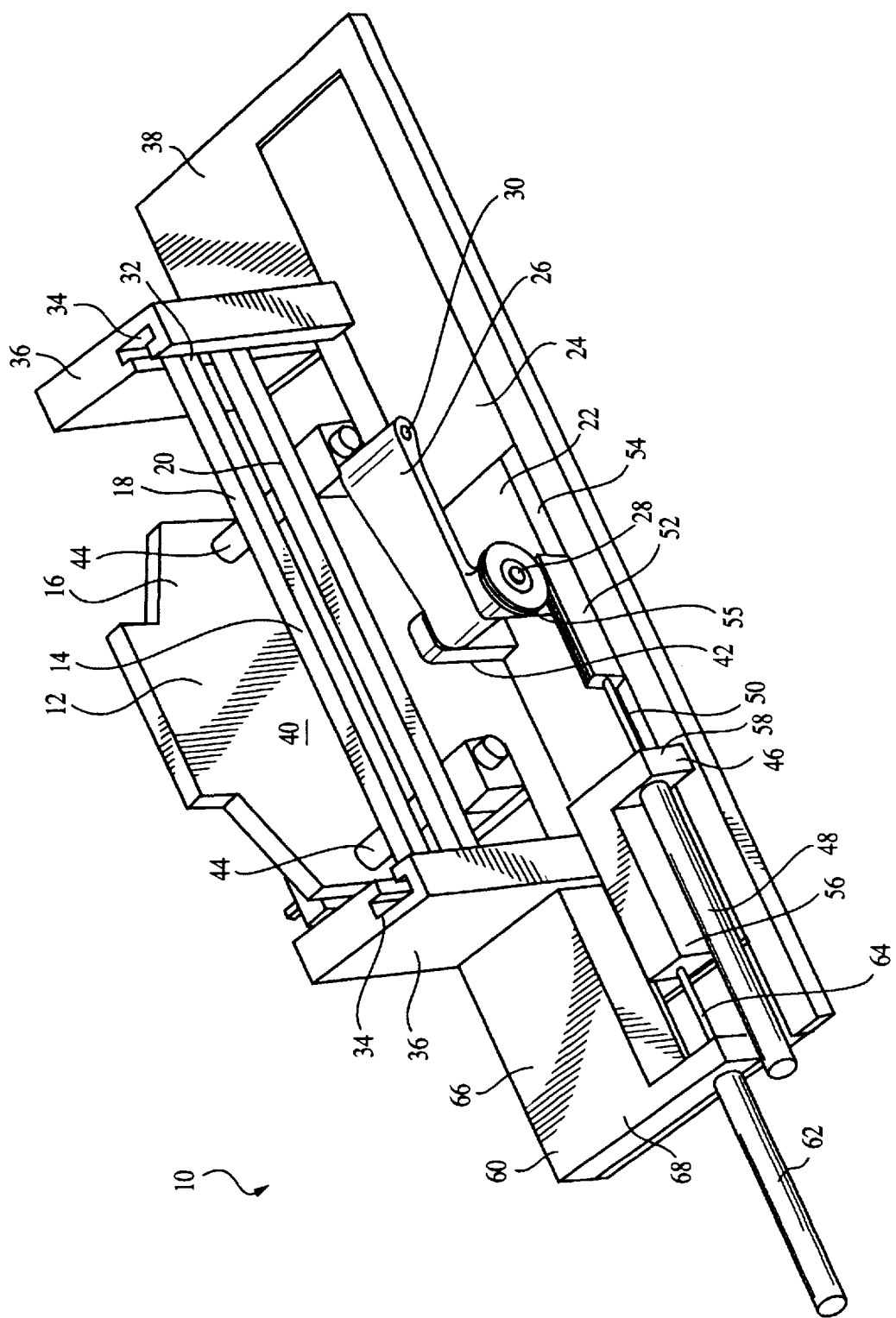
FIG. 1 is a front perspective view of a preferred embodiment of a medical device positioner.
Figure 2:
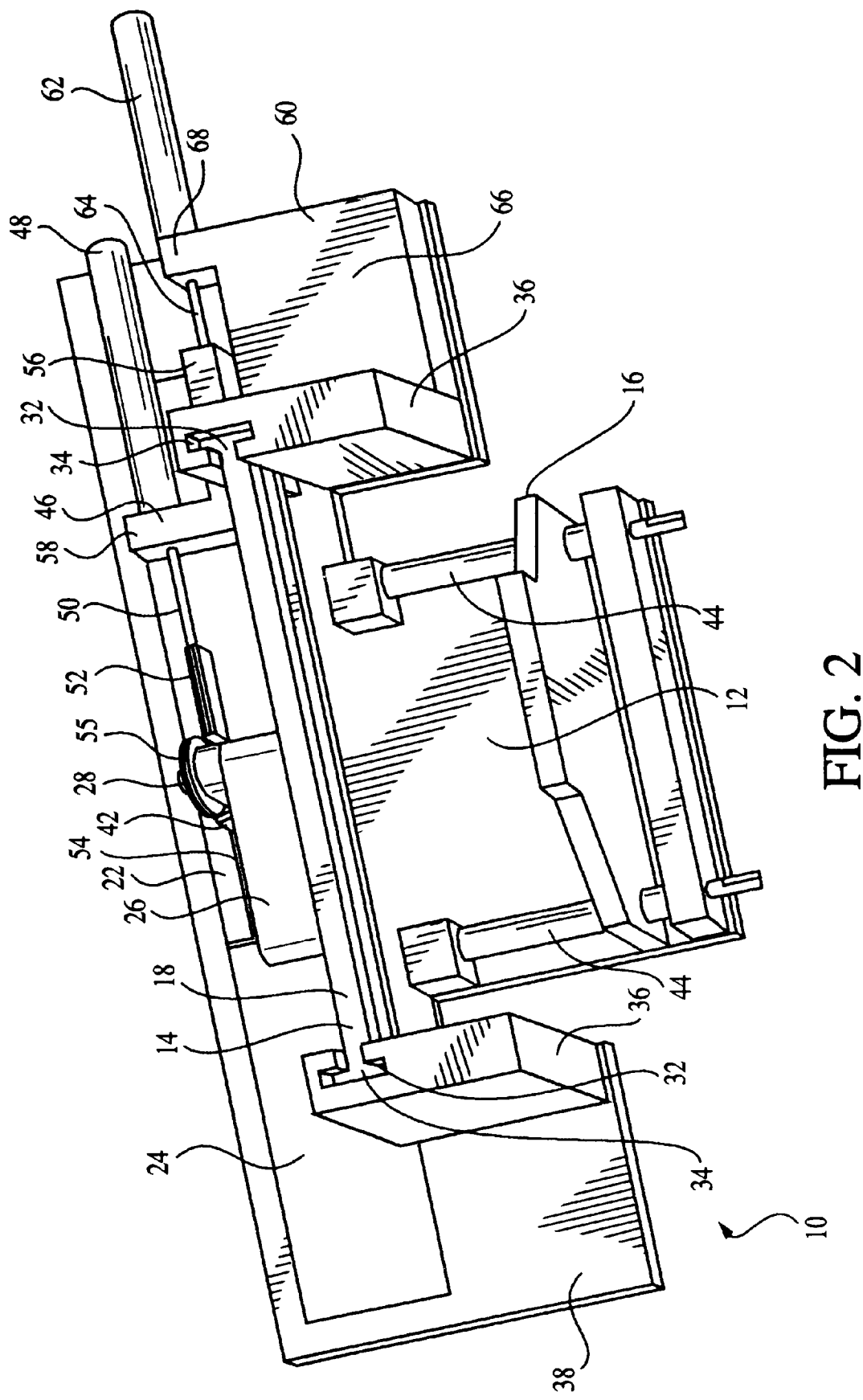
FIG. 2 is a rear perspective view of a preferred embodiment of the medical device positioner of FIG. 1.

Looking to FIGS. 1 and 2 of the drawings, a particularly preferred embodiment of the medical device positioner is designated generally by the reference numeral 10. The positioner 10 includes a clamp 12 for grasping a portion of a human body, with the clamp 12 including opposable first and second grasping elements 14 and 16 (wherein the first grasping element 14 includes first and second members 18 and 20 which may be variably spaced with respect to each other, and the second grasping element 16 is provided by a plate which is translatable towards the first and second members 18 and 20 of the first grasping element 14); a carriage 22 which is movable along a carriage path 24 adjacent the first grasping element 14; and a positioning arm 26 which is rotatably mounted to the carriage 22 at a pivot 28, and which has a medical device mount 30 (best seen in FIG. 1) spaced from the pivot 28 so that a medical device situated within the mount 30 may be swung to various locations adjacent the first and second members 18 and 20 of the first grasping element 14 of the clamp 12. Thus, a portion of a human body may be firmly maintained between the first and second grasping elements 14 and 16 of the clamp 12 with the first and second members 18 and 20 of the first grasping element 14 being appropriately spaced to allow a medical device access to the grasped portion of the human body.

The positioner 10 is preferably made of materials which do not interfere with the operation or imaging ability of medical imaging devices. As an example, where the portion of the human body within the clamp 12 is to be imaged in a magnetic resonance imaging (MRI) device, the positioner 10 may be made of plastic or other nonmagnetic materials such as 300 series stainless steel, copper, ceramics, or composites of the foregoing. However, the positioning arm 26 or other portions of the positioner 10 may (and preferably do) include materials which are visible when imaged so a user may determine the position and/or orientation of a medical instrument with respect to the clamped portion of the body. For example, the medical device mount 30 and/or the first and second members 18 and 20 of the first grasping element 14 may include markers which are detected by the imaging device and which are visible on its generated image.

The carriage 22 and positioning arm 26 of the positioner 10 are preferably positioned by actuators which also do not interfere with the accurate use of the imaging device. For example, where an MRI device is used for imaging, non-electromechanical actuators or other actuators which do not generate and/or interfere with magnetic fields are preferably used, such as the hydraulic actuation system illustrated in FIGS. 1 and 2 at 48 and 62 (as discussed in greater detail later in this document). The actuators are preferably remotely controlled so that an operator outside the imaging device may actuate the positioner 10 and simultaneously view the location of the positioner 10 and the position of a medical device therein with respect to the clamped body portion.

The positioner 10 may be better understood if the foregoing components are discussed in greater detail. The clamp 12 is intended to firmly grasp the exterior of the body portion which is to be imaged, and which is to be operated upon by the medical device. The clamp 12 also preferably applies some degree of compression to the body portion so that any semi-mobile structures within the body portion will be fixed in place; for example, a hard breast tumor may be pushed by a biopsy needle within a breast (rather than being penetrated) unless the breast is firmly grasped to prevent migration of the tumor. As previously noted, the first grasping element 14 of the clamp 12 includes first and second members 18 and 20 which have variable spacing. The first and second members 18 and 20 are each defined by rectangular bars having T-shaped ends 32 which slide within complementary slots 34 defined within a pair of opposing towers 36 mounted on a common positioner base 38. The materials, configuration, and sizing of the bar ends 32 are such that the first and second members 18 and 20 slide within the slots 34 with slight resistance, so that the first and second members 18 and 20 remain in a user-selected position within the slots 34. Additionally, the first and second members 32 are always maintained in a parallel orientation. Note that the positioner 10 is illustrated as including slots in the positioner base 38 between the towers 36 and the clamp 12 to accommodate the insertion of MRI coils within these slots.

The second grasping element 16 is provided in the form of a plate which may translate towards the first grasping element 14 (i.e., towards the first and second members 18 and 20) in a direction termed the grasping direction. The grasping surface 40 of the second grasping element 16 (i.e., the surface which engages the clamped body portion, visible only in FIG. 1) is preferably always maintained in a parallel orientation with respect to a plane defined by the first and second members 18 and 20. The parallel orientation is provided by having the second grasping element 16 travel on a pair of screws 44 which extend through its opposing sides and which are rotatably anchored to the positioner base 38, so that rotation of the screws 44 drives the second grasping element 16 in the grasping direction towards or away from the first grasping element 14. The second grasping element 16 preferably translates toward the first grasping element 14 along a path situated between the towers 36 so that the first and second members 18 and 20 of the first grasping element 14 can span the entire length of the grasped body portion. As will be apparent from the following discussion, this allows the positioning arm 26 (and the device mount 30 thereon) to be situated at any desired location along the length of the grasped body portion.

The carriage 22 slides along the carriage path 24 on the side of the first grasping element 14 opposite the second grasping element 16, with the carriage path 24 being oriented parallel to the first and second members 18 and 20 of the first grasping element 14. The carriage path 24 is preferably defined within the positioner base 38 as a dovetailed slot, wherein the carriage 22 is provided with edges which fit complementarily therein to prevent dislodgment in the dimensions perpendicular to the carriage path 24. The positioning arm 26 and carriage 22 will therefore avoid tipping when a medical device situated within the mount 30 is actuated to engage the clamped body portion.

As best seen in FIG. 1, a pair of clevis arms 42 extend from the carriage 22 to receive the positioning arm 26 therebetween. The pivot 28 then extends between the clevis arms 42 and through the positioning arm 26 so that the positioning arm 26 is rotatably mounted on the carriage 22 about the pivot 28. The axis of the pivot 28 is oriented perpendicular to the direction in which the carriage 22 moves along the carriage path 24, and also perpendicular to the first and second grasping elements 14 and 16, but is parallel to the grasping direction in which the second grasping element 16 moves with respect to the first grasping element 14. Thus, the positioning arm 26 swings in a plane parallel to the first and second members 18 and 20 of the first grasping element 14, allowing the positioning arm 26 to traverse a greater area of the body portion maintained within the clamp 12.

The medical device mount 30 is preferably situated at the very end of the positioning arm 26 opposite the pivot 28, as best seen in FIG. 1, so that the positioning arm 26 does not have excess length that might interfere with other objects that may be present in a constrained space in which the positioner 10 might be used. In FIG. 1, the medical device mount 30 is depicted as an aperture suitable for the insertion of a biopsy needle or similar device, with this aperture having an axis parallel to the pivot 28 (and thus perpendicular to the plane of the first grasping element 14 of the clamp 12). It is therefore noted that in the preferred positioner 10 illustrated in FIGS. 1–2, the motion of the carriage 22, positioning arm 26, and second grasping element 16 of the clamp 12, and the orientation of a medical device within the mount 30, are all aligned within orthogonal directions/planes, which simplifies coordinate calculations and motion control when the positioner 10 is computer-controlled (as discussed elsewhere in this document).

The foregoing components are preferably provided on the positioner base 38 as a stand-alone assembly, as illustrated in the Figures, so that the positioner 10 may be placed in and removed from different medical imaging devices when desired, and may also be more easily situated and oriented within any particular medical imaging device as desired. It should be appreciated that the positioner 10 has been designed for efficient and accurate positioning within a particularly compact space, such as that provided within the tunnel of common MRI devices.

The foregoing arrangement is by itself suitable for use in the same manner that prior positioners are used, i.e., the positioner 10 may be left alongside the patient during imaging, the positioning arm 26 and the medical device borne therein may be manually positioned in accordance with the results of an imaging process, and the process of imaging and repositioning can be performed iteratively until the medical device is suitably positioned. However, because the manual iterative process of imaging and repositioning the positioning arm 26 can be time-consuming, it is particularly desirable to provide the positioner 10 with actuators so that the carriage 22 and positioning arm 26 thereon may be repositioned during the imaging process so that imaging and repositioning can occur simultaneously. Thus, the following arrangement is used in particularly preferred embodiments of the invention.

An arm actuator anchor 46 is provided on the carriage 22 so that it may travel thereon. An arm actuator 48 is then attached to the arm actuator anchor 46. The arm actuator 48, which is preferably provided in the form of a fluid actuator such as a hydraulic cylinder (with hoses and/or other fittings not shown in the Figures), has an arm actuator rod 50 extending therefrom which is linearly driven by the arm actuator 48. The arm actuator rod 50 extends through the arm actuator anchor 46 so that actuation of the arm actuator 48 will drive the arm actuator rod 50 with respect to the arm actuator anchor 46 and carriage 22. The end of the arm actuator rod 50 opposite the arm actuator anchor 46 is affixed to an elongated driving link 52 which moves with respect to the carriage, preferably within a driving link slot 54 wherein the driving link 52 is complementarily fit so that it may only move parallel to the carriage path 24 (as by dovetailing the driving link slot 54 and appropriately forming the driving link 52 to slide therein). The driving link 52 is linked to the positioning arm 26 and/or its pivot 28 so that actuation of the arm actuator 48, and motion of its arm actuator rod 50, will act on the positioning arm 26 and/or its pivot 28 to rotate the positioning arm 26. In the preferred embodiment of the positioner 10 illustrated in the Figures, the driving link 52 is formed as a toothed rack which cooperates with a pinion 55 affixed to the pivot 28 to rotate the positioning arm 26 when the driving link 52 is moved. The arm actuator anchor 46 is formed as an L-shaped block having its head 56 adjacent to one end of the carriage 22 and its base 58 nearer the positioning arm 26, and having the arm actuator rod 50 extending through its base 58, so that much of the length of the arm actuator 48 is carried on the carriage 22 for sake of a compact design. The carriage 22 therefore allows positioning of a medical device along one axis (the axis parallel to the direction of the carriage path 24), with the swinging positioning arm 26 then providing further positioning in this direction as well as in an orthogonal direction (along the axis perpendicular to the direction of the carriage path 24 and to the first grasping element 14). The use of a swinging positioning arm 26 is believed to be particularly beneficial because it achieves positioning in two degrees of freedom within a plane parallel to the first grasping element 14 in an extremely compact and easy-to-control mechanism. Additionally, the use of the driving link 52 also allows significant rotation of the positioning arm 26 with only a short linear input from the arm actuator 48.

The carriage 22 is driven by use of a similar arrangement. A carriage actuator anchor 60 is provided on the positioner base 38 near one of its ends, and the carriage actuator anchor 60 has a carriage actuator 62 attached thereon. As with the arm actuator 48, the carriage actuator 62 is preferably provided in the form of a fluid actuator such as a hydraulic cylinder (with hoses and/or other fittings not shown in the Figures), and has a carriage actuator rod 64 extending therefrom which is linearly driven by the carriage actuator 62. The carriage actuator rod 64 extends through the carriage actuator anchor 60 so that actuation of the carriage actuator 62 will drive the carriage actuator rod 64 with respect to the carriage actuator anchor 60 and the positioner base 38. The end of the carriage actuator rod 64 opposite the carriage actuator anchor 60 is affixed to the head 56 of the arm actuator anchor 46 so that actuation of the carriage actuator 62, and motion of its carriage actuator rod 64, will act on the arm actuator anchor 46 to drive the carriage 22 along the carriage path 24. The carriage actuator anchor 60 is formed as an L-shaped block having its head 66 affixed to the positioner base 38 and its base 68 located along the carriage path 24, and having the carriage actuator rod 64 extending through its base 68, so that the carriage 22 translates along the carriage path 24 adjacent to the base 68. The base 68, while situated above the carriage path 24, does not extend so far into the carriage path 24 that it interferes with the motion of the arm actuator 48, which translates adjacent to the base 68. As a result of this arrangement, the carriage actuator anchor 60 does not significantly diminish the range of motion of the carriage 22 along the carriage path 24.

The positioner 10 is preferably configured so that the carriage 22 is easily removed for cleaning and/or sterilization. This may be achieved by removably affixing the carriage actuator anchor 60 to the positioner base 38, as by the use of threaded fasteners, so that the carriage actuator anchor 60 may be removed therefrom. The carriage 22 may then be slidably removed (along with the carriage actuator anchor 60) from the carriage path 24, which extends to the end of at least one side of the positioner base 38. The end of the carriage actuator rod 64 opposite the carriage actuator anchor 60 is preferably threaded within the head 56 of the arm actuator anchor 46 so that it may be rotated and removed therefrom, thereby allowing detachment of the carriage 22 from the carriage actuator anchor 60 and carriage actuator 62. Similarly, the arm actuator anchor 46 is preferably removably affixed to the carriage 22 to allow its removal therefrom, and the end of the arm actuator rod 50 is threaded within the driving link 52 to allow removal of the arm actuator anchor 46 and arm actuator 48 from the carriage 22 when desired. The driving link 52 may be removed from the carriage 22 by sliding it out of one end of the driving link slot 54, which preferably extends along the entire length of the carriage 22.

Hydraulic actuation of the positioner 10 is preferred for accuracy of control, and additionally hydraulic systems which are usable within an MRI device may be more readily constructed than electromechanical actuators suitable for such use. A particularly advantageous arrangement is to provide master cylinders which drive the arm actuator 48 and carriage actuator 62 as slave cylinders. The master cylinders may be situated adjacent the controls of an MRI device, and the positioner 10 may be situated within the MRI device so that the carriage 22 and positioning arm 26 may be remotely controlled from outside the MRI device. Such control may be manual, as by manually actuating the master cylinders with screw wheels or similar structures suitable for actuation by hand, or by semiautomatic or automatic control, as by actuating the master cylinders by human input to software which actuates the master cylinders (as by use of stepping motors). However, it is emphasized that these are only preferred arrangements and many other modes of actuation could be employed instead.

The foregoing positioner 10 may be constructed in operable condition within a 16 inch×4 inch×7 inch envelope, which is the approximate size of the available space within the tunnel of an MRI device adjacent to a patient resting in a support cradle.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. Following is an exemplary list of such modifications.

First, the clamp 12 may assume a wide variety of configurations other than the one previously described and illustrated. The screws 44, rather than being independently manually actuated, may be linked by a system of pulleys, gears, or other structures so that rotation of one of the screws 44 will result in rotation of the other. Rather than utilizing the screws 44, the second grasping element 16 might travel along slides or rails which allow a user to anchor the second grasping element 16 on the positioner base 38 a desired distance away from the first grasping element 14. As another possibility, the second grasping element 16 might travel within dovetail slots or other tracks within the second grasping element 16. Also, the first grasping element 14 might be allowed to move on the positioner base 38 towards the second grasping element 16 in addition to or instead of the motion of the second grasping element 16.

Second, it should be understood that if greater grasping and/or compression of a body portion is needed, additional members apart from first and second members 18 and 20 may be fit within the slots 34 of the towers 36. For example, one or more members configured similarly to the first and second members 18 and 20 may be added to the slots 34 to increase the effective area of the first grasping element 14. Alternatively, one or more of the first and second members 18 and 20 may be removed and replaced with a member having a different size.

Third, apart from remote actuation of the carriage 22 and positioning arm 26, the clamp 12 could also be remotely actuated. However, this is generally unnecessary because there is usually no need to adjust clamping once clamping is initially performed. However, if remote actuation of the clamp 12 is desired, there is a number of ways in which this may be done, as by providing a gear box, sprocket/chain, or timing belt/pulley arrangement whereby both screws 44 are simultaneously rotated to drive the second grasping element 16 along the grasping direction when rotational input is provided to only one of the screws 44. A timing belt and pulley are particularly preferred for sake of ease of manufacture and lower expense, particularly where nonmagnetic materials must be used for the components of the clamp 12.

Fourth, apart from having the carriage 22 slide within a complementarily-shaped carriage path 24, other arrangements are possible; for example, the carriage 22 could ride on a track elevated above the surface of the positioner base 38 (e.g., on cylindrical rods or screws). However, it is particularly preferred to have the carriage 22 ride within the dovetailed carriage path 24 because this arrangement is particularly resistant to tipping and unwanted displacement of the carriage 22, while at the same time providing a low profile for the carriage 22, which is important where the positioner 10 is to be used in enclosed spaces (such as the tunnel of an MRI device).

Fifth, the positioning arm 26 may be rotated by means other than by use of the driving link 52 and pinion 55. As an example, the arm actuator rod 50 may be pivotally and/or slidably mounted directly to the positioning arm 26 at a point spaced away from the pivot 28 whereby extension and retraction of the arm actuator rod 50 will result in pivoting of the positioning arm 26. However, this arrangement is not as compact, and it additionally requires precise control of the arm actuator 48 to properly position the positioning arm 26. As alternatives, the driving link 52 may frictionally engage a wheel which is affixed to the positioning arm 26 in place of the pinion 55; the driving link 52 may be pivotally engaged within a slot provided in a wheel or lever arm extending from the positioning arm 26 and/or its pivot 28; or other arrangements may be used to transform the linear input of the arm actuator 48 to rotary motion of the arm 26.

Sixth, other actuators are possible for use in the positioner 10 apart from the arm actuator 48 and carriage actuator 62. As previously noted, it is generally preferable to avoid electromechanical actuators (such as stepping motors with worm gears, electromagnetic slides, etc.) because such actuators are generally incompatible for use within MRI devices, or where such devices are compatible, they can be costly. Thus, fluid (hydraulic or pneumatic) actuation is particularly preferred, as by hydraulic or pneumatic cylinders, chambers, or bladders which are capable of providing motion inputs. Hydraulic actuation is generally preferred over pneumatic actuation because the use of an incompressible motive fluid will help avoid unwanted displacement of the positioning arm 26 and carriage 22. If MRI-compatible stepping motors or other electromechanical actuators are desired, these may be obtained from providers such as Daum GmbH, Schwerin, Germany and/or Daum Corporation, Chicago, Ill., USA.

Seventh, other modes of removal of the carriage 22 from the positioner 10 are possible. As an example, if the carriage path 24 extends across the entire length of the positioner base 38, the carriage 22 may be removed by simply unthreading the end of the carriage actuator rod 64 from the head 56 of the arm actuator anchor 46, and the carriage 22 may slide out of the carriage path 24 at the end of the positioner base 38 opposite the carriage actuator anchor 60.

The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A positioner for medical devices comprising:
   a. a clamp including:
      (1) a first grasping element including first and second members having variable spacing therebetween, and
      (2) a second grasping element,
         wherein the grasping elements have adjustable spacing therebetween, whereby at least one of the grasping elements may be moved toward another of the grasping elements to secure a portion of a human body therebetween,
         and wherein the first grasping element is interposed between the carriage path and the second grasping element;
   b. a carriage, the carriage being movable along a carriage path adjacent to the clamp;
   c. a positioning arm having a pivot and a medical device mount spaced from the pivot, wherein the positioning arm is rotatably mounted to the carriage at the pivot to swing adjacent the clamp in a first plane which is at least substantially parallel to a second plane defined between the first and second members of the first grasping element;
whereby a medical device within the medical device mount is positionable in various locations with respect to the clamp.

2. The positioner of claim 1 wherein at least one of the first and second grasping elements is defined by a pair of parallel bars.

3. The positioner of claim 1 further comprising a positioner base whereupon the carnage is slidably mounted, wherein at least one of the first and second members may be adjustably positioned with respect to the positioner base.

4. The positioner of claim 1 further comprising a positioner base whereupon the clamp is mounted and the carriage is translatably mounted, wherein:
   a. the carriage bears an arm actuator thereon, whereby actuation of the arm actuator moves the positioning arm with respect to the carriage;
   a. the positioner base bears a carriage actuator thereon, whereby actuation of the carriage actuator moves the carriage with respect to the positioner base.

5. The positioner of claim 4 further comprising an arm actuator anchor attached between the carriage and the arm actuator, and also attached between the carriage actuator and the carriage.

6. The positioner of claim 1 wherein the positioning arm is rotatably driven by a toothed rack which moves with respect to the carriage.

7. The positioner of claim 6 wherein the toothed rack is driven by a fluid actuator with respect to the carriage.

8. A positioner for medical devices comprising:
   a. a clamp including first and second grasping elements spaced by an adjustable gap, wherein the grasping elements may be secured about a portion of a human body;

b. a carriage, the carriage being translatable along a carriage path adjacent to the clamp;

c. a positioning arm rotatably mounted to the carriage at a pivot, the positioning arm bearing a medical device mount spaced from the pivot, wherein the positioning arm may swing about the pivot in a plane parallel to the carriage path and adjacent to the clamp;

d. a positioner base whereupon the carriage path and clamp are situated, and wherein the carriage is moved with respect to the positioner base by fluid actuation.

9. The positioner of claim 8 wherein the first grasping element includes first and second members having variable spacing therebetween, and the first grasping element is interposed between the carriage and the second grasping element.

10. The positioner of claim 9 wherein the second grasping element is at least substantially parallel to a plane defined by the first and second members.

11. The positioner of claim 9 wherein the positioning arm swings in a first plane which is at least substantially parallel to a second plane defined by the first and second members.

12. The positioner of claim 8 wherein the positioning arm is moved with respect to the carriage by fluid actuation.

13. The positioner of claim 12 wherein the positioning arm is rotatably driven by a toothed rack.

14. A positioner for medical devices comprising:

a. a positioner base;

b. a clamp mounted on the positioner base, the clamp including first and second grasping elements wherein the second grasping element is movable toward the first grasping element along a grasping direction to secure a portion of a human body between the first and second grasping elements;

c. a carriage slidably mounted along a carriage path on the positioner base, the carriage path being adjacent to the first grasping member and being oriented at least substantially perpendicular to the grasping direction;

d. a positioning arm rotatably mounted to the carriage at a pivot, the positioning arm bearing a medical device mount spaced from the pivot, wherein the positioning arm may swing about the pivot in a plane oriented at least substantially parallel to the carriage path and at least substantially perpendicular to the grasping direction.

15. The positioner of claim 14 wherein:

a. the first grasping element is interposed between the second grasping element and the carriage, and b. the first grasping element includes first and second members wherein at least one of the members is movable with respect to the other of the members in a plane oriented at least substantially parallel to the plane wherein the positioning arm swings.

16. The positioner of claim 1 further comprising a compact and portable positioner base upon which the clamp is mounted and along which the carriage moves.

17. The positioner of claim 8 wherein the positioner is compact and portable whereby a user may readily lift the positioner by its positioner base and move it to different locations.

18. The positioner of claim 14, wherein the carriage is slidably moved with respect to the positioner base by fluid actuation.

19. The positioner of claim 14 wherein the positioning arm is swung about the pivot by fluid actuation.

20. The positioner of claim 14 wherein the positioner is compact and portable whereby a user may readily lift the positioner by its positioner base and move it to different locations.

21. A positioner for medical devices comprising:

a. a clamp including first and second grasping elements, at least one of the grasping elements being movable towards the other in a grasping direction to secure a portion of a human body therebetween;

b. a carriage, the carriage being movable along a carriage path extending adjacent to the first grasping element;

c. a positioning arm which swings about a pivot situated on the carriage; and d. a medical device mount on the positioning arm spaced from the pivot, wherein swinging the positioning arm swings the medical device mount within a first plane, the first plane being (1) parallel to the carriage path, and (2) spaced from the clamp.

22. The positioner of claim 21 wherein the first plane is oriented at least substantially perpendicular to the grasping direction.

23. The positioner of claim 22 wherein the first grasping element is situated between the first plane and the second grasping element.

24. The positioner of claim 21 wherein at least one of the first and second grasping elements is defined by first and second members having adjustable spacing therebetween.

25. The positioner of claim 24 wherein the first and second members are adjustable along a plane oriented at least substantially perpendicular to the grasping direction.

26. The positioner of claim 21 wherein the positioning arm is moved with respect to the carriage by fluid actuation.

27. The positioner of claim 21 further comprising a compact and portable positioner base upon which the clamp is mounted and along which the carriage moves.

28. A positioner for medical devices comprising:

a. a positioner base;

b. a clamp affixed to the positioner base, the clamp including first and second grasping elements, at least one of the grasping elements being movable towards the other in a grasping direction to secure a portion of a human body therebetween;

c. a medical device mount movably connected to the positioner base, c. actuators driving movement of the medical device mount with respect to the positioner base, the actuators being capable of remote actuation;

wherein such remote actuation is restrained to:

(1) translating the medical device mount alongside the first grasping element, and (2) swinging the medical device mount in a plane oriented at least substantially perpendicular to the grasping direction.

29. The positioner of claim 28 wherein at least one of the first and second grasping elements is defined by first and second members having adjustable spacing therebetween.

30. The positioner of claim 29 wherein the first and second members are adjustable along a plane oriented at least substantially perpendicular to the grasping direction.

31. The positioner of claim 28 wherein the positioner is compact and portable whereby a user may readily lift the positioner by its positioner base and move it to different locations.

32. The positioner of claim 28 wherein the actuators are fluid actuators.

* * * * *